United States Patent [19]

Jones, Jr. et al.

[11] 4,313,916

[45] Feb. 2, 1982

[54] PROCESS FOR THE PURIFICATION OF NON-REACTING GASES

[75] Inventors: Robert A. Jones, Jr., South Charleston; Arthur E. Marcinkowsky, Charleston; George E. Keller, II, South Charleston, all of W. Va.

[73] Assignee: Union Carbide Corporation, New York, N.Y.

[21] Appl. No.: 141,141

[22] Filed: Apr. 17, 1980

Related U.S. Application Data

[63] Continuation-in-part of Ser. No. 89,316, Oct. 31, 1979, abandoned, which is a continuation-in-part of Ser. No. 38,736, May 14, 1979, abandoned.

[51] Int. Cl.$^3$ ............................................. G01D 53/34
[52] U.S. Cl. ................................... 423/226; 423/232; 423/234; 423/235; 423/236; 423/240; 423/243; 423/262; 423/351; 423/415 A; 423/579; 423/648 R; 585/854
[58] Field of Search ............... 423/226, 232, 234, 243, 423/351, 415 A, 225, 648 R, 240, 235, 236, 262, 579; 55/73, 78; 585/833, 854, 853; 252/191

[56] References Cited

U.S. PATENT DOCUMENTS

| | | | |
|---|---|---|---|
| 642,782 | 2/1900 | Buck | 423/236 |
| 1,029,528 | 6/1912 | Bosch et al. | 423/235 |
| 1,290,244 | 1/1919 | Kramers | 423/232 X |
| 1,519,932 | 12/1924 | Reich | 423/226 |
| 1,717,761 | 6/1929 | Claude | 423/226 |
| 1,912,833 | 6/1933 | Fairlie | 423/235 |
| 2,146,353 | 2/1939 | Rosebaugh | 585/853 |
| 2,177,068 | 10/1939 | Hutchinson | 423/226 |
| 2,185,332 | 1/1940 | Crampton | 252/5 |
| 2,445,064 | 7/1948 | Hall et al. | 252/192 |
| 2,742,517 | 4/1956 | Fusco | 585/833 |
| 3,897,227 | 7/1975 | Giammako | 55/68 |
| 4,000,246 | 12/1976 | Wolles | 423/230 |
| 4,035,167 | 7/1977 | Starks | 55/57 |

FOREIGN PATENT DOCUMENTS

1240753  7/1971  United Kingdom ................ 423/575

*Primary Examiner*—Earl C. Thomas
*Attorney, Agent, or Firm*—Gerald R. O'Brien, Jr.

[57] ABSTRACT

A process is disclosed for the purification of an inert or non-reacting gas such as lower mono-olefins by the removal of trace amounts of reacting impurities such as carbon dioxide therefrom, comprising passing said gas through an essentially non-aqueous liquid solution of alkali or alkaline earth metal hydroxides and/or weak acid salts and certain selected liquid polyhydric alcohols.

12 Claims, 5 Drawing Figures

PROCESS FOR THE PURIFICATION OF NON-REACTING GASES

This is a continuation-in-part of our prior copending application Ser. No. 089,316, filed Oct. 31, 1979, and entitled "Process for the Purification of Olefin Gases", now abandoned; which is, in turn, a continuation-in-part of prior copending application Ser. No. 038,736, filed May 14, 1979, and entitled "Process for the Purification of Olefin Gases", and now abandoned.

The present invention relates to the purification of certain gas streams and, more particularly, to such purification of such gas streams by the removal of minute quantities of impurities therefrom.

The reaction of basic alkali or alkaline earth metals per se, or as hydroxides or weak acid salts, with acids is known chemistry. Such chemistry, as elementary as it may seen, has become the foundation of significant commercial practices. For example, in the fluid of purifying industrial gas streams, such as hydrogen, carbon monoxide, air, oxygen, nitrogen, argon, helium, lower monoolefins, lower diolefins, and the like, beds or suspensions of solid particles of sodium or potassium hydroxides have been employed to remove gross amounts of acid gases. Such processes were discovered to be relatively inefficient in removing trace amounts of impurities, such as hydrogen sulfide, carbon dioxide, carbonyl sulfide, sulfur dioxide and mercaptans and the like from such streams. Indeed, such alkali metal hydroxides have been taught for use as absorbents to separate acetylene from ethylene, see U.S. Pat. No. 2,742,517.

There is described in U.S. Pat. No. 2,185,332, patented Jan. 2, 1940, a process for dehydrating and acid sequestering of refrigeration systems by supplying to the refrigeration systems of an alkali alcoholate, particularly sodium methylolate. The alcoholate is supplied to the system to remove water by a methathysis reaction which yields the alkali hydroxide, such as sodium hydroxide. Sodium hydroxide, or caustic, is left in the system. The consequences are obvious. Caustic is a corrosive agent and its presence in the refrigerant gas cannot be beneficial in the long run. In addition, the patent speaks of removing acids as well. For example, hydrogen chloride, presumably as hydrochloric acid, is converted to sodium chloride. It may be that HCl is more corrosive than NaCl, but certainly NaCl is not advantageous to leave in the refrigerant gas. Thus, this patent utilizes known chemistry to solve one problem, but the patent's process creates other problems. As bad a problem that water may be, caustic formation cannot be perceived as significant improvement.

U.S. Pat. No. 2,177,068, patented Oct. 24, 1939, is concerned with the treatment of natural gas to remove water and acid gases. The patent utilizes polyhydric alcohols in combination with amines, e.g., alkanol amines, for this purpose. The patent acknowledges that it was old, even then, to use such amines to remove acid gases, and polyols have long been known as humectants.

In the above two processes, the gases being treated are saturated hydrocarbons whose inertness have been well established. The impurities being removed do not adversely affect the function of these gases, they only adversely affect the environment in which the gases are used.

In any event, the process of this patent suffers from the reliance upon amines to extract the acid gases. These amine systems are known to be corrosive.

The evolution of industrial gas purification has followed the improvements in impurity detection. With improved analytical procedures that can be applied to evaluation of industrial gas streams has come the need for superior processes for the removal of newly detectable impurities.

As employed herein, the terms "non-reacting" and "inert gases" refer to those industrial gases which are capable of treatment in accordance with the process of the invention without reacting with the selected alkali/polyhydric alcohol solutions defined below.

It is generally understood that olefins, due to their manner of production, storage and/or handling, may typically contain in trace amounts in the range of parts per million of some or all of the following impurities: water vapor, hydrogen sulfide, carbon dioxide, carbonyl sulfide, sulfur dioxide, and mercaptans. Many commercial syntheses require an olefin feed having below 1, and preferably below 0.5 ppm of each of the impurities.

For example, in order to make suitable grade ethylene for the production of certain grades of polyethylene, small concentrations of $CO_2$ (of approximately 10–25 ppm) in the olefin feed have to be reduced to less than 1 ppm. One present practice uses a caustic pellet absorber bed. Two major problems associated with this procedure are: (i) only about 3 percent of the NaOH present in the bed is converted to $Na_2CO_3$ (via $2NaOH + CO_2 \rightleftharpoons Na_2CO_3 + H_2O$); and (ii) after the outer coat of the pellet is converted to the carbonate, the water generated can cause particle agglomeration and bridging which in turn causes channeling and finally complete solidification of the bed. The latter is a particularly difficult problem because the bed contents at times have had to be removed manually. An aqueous caustic solution has been proposed as an alternative. One problem with this approach is that the water vapor from the solution is introduced into the ethylene, thus necessitating zeolite water-adsorption beds which: (i) would be large and costly to install; and (ii) would be expensive to regenerate.

The process of this invention employs a liquid, essentially non-aqueous treating medium, that is, the medium typically does not contribute more water to the gas undergoing treatment. The liquid treating medium exhibits (i) a high capacity (i.e., solubility) for the alkali, (ii) a very low vapor pressure, (iii) when combined with the alkali, the system is chemically stable, and (iv) a sufficiently low viscosity to permit proper wetting of the gas being treated.

The process of this invention is the use of an alkali (or alkaline earth) metal/liquid polyhydric alcohol solution to remove the aforedefined trace impurities, and, in particular, to simultaneously remove substantially all of the deleterious trace impurities when they are present, rather than just a single impurity, as has been prior art approach.

Thus, in accordance with the present invention, a process is provided for the purification of an industrial gas stream of hydrogen, carbon monoxide, air, nitrogen, oxygen, helium, argon, mono-olefins having from two to five carbon atoms per molecule, diolefins having four or five carbon atoms per molecule, paraffins, or acetylenes, by the removal of trace amounts of reacting impurities, introduced therein prior to or during a process for the production or treatment of said gas, and including, for example, hydrogen sulfide, carbon dioxide, carbonyl sulfide, sulfur dioxide, hydrogen chloride, hydrogen cyanide, nitric acid, and mercaptans. This is accomplished by contacting said gas, at a temperature between about 15° and 100° C., with an essentially non-aqueous liquid solution comprising from about 0.5 to 15 weight percent of alkali or alkaline earth metal, measured as its hydroxide or weak inorganic acid salts, in a liquid aliphatic polyhydric alcohol having a carbon to oxygen ratio of one (1) to five (5), and at least two (2) oxygens thereof being separated by not more than two (2) sequential carbon atoms.

In addition, the process of this invention comprises continuously feeding an industrial gas stream, as described, to a body of liquid alkali/polyhydric alcohol solution, as described herein, maintained at a temperature between about 15° and 100° C., in which the gas stream is removed from contact with the body into an atmosphere in which the partial pressure of water therein is insufficient to significantly increase the water concentration in the stream. In the preferred embodiment, the water concentration of the stream removed from the liquid body and the atmosphere is less than was contained in the stream fed to the body.

The "alkali and alkaline earth metals" referred to herein are those from groups IA, and IIA of the Period Table of Elements; specifically they are: lithium, sodium, potassium, rubidium, cesium, magnesium, calcium, strontium, and barium. As discussed hereinbelow, the preferred alkali metals are sodium and potassium, with potassium constituting the most preferred metal for the practice of the process of the present invention. For purposes of discussion only, the term "alkali" shall mean alkali metal and alkaline earth metal as hereinabove defined.

For brevity in description and for convenience, the process of the invention is primarily discussed hereinbelow in connection with the removal of trace amounts of impurities of the group set forth hereinabove from ethylene gas.

The alkali value provided in the polyhydric alcohol solution may be obtained from the hydroxides and weak inorganic acids of the alkali or alkaline earth metals.

The polyhydric alcohol includes glycerol and alkylene glycols, for example, those having up to twelve carbon atoms (such as: ethylene glycol, diethylene glycol, triethylene glycol, tetraethylene glycol, propylene glycol, dipropylene glycol, 1,2-butylene glycol, di-1,2-butylene glycol, and the like), and alkylene oxide adducts. Such alkylene oxide adducts are made by reacting the alkylene oxide with a polyol such as the aforementioned glycols, glycerol and other triols (for example, 1,2,6-hexane triol, monomethyl ether of erythritol, and the monomethyl ether of pentaerythritol). Ethylene oxide and propylene oxide adducts of the polyols are preferred. Most preferred of the adducts are the ethylene oxide adduct, alone or reacted with propylene oxide.

The process of the present invention is for the purification of a gas stream which contains as its major component an inert gas which does not react chemically (non-reacting) with the liquid alkali/polyhydric alcohol solution selected for the process and which stream contains, in trace amounts, a minor component which chemically reacts with the same liquid alkali/polyhydric alcohol solution. Examples of the non-reacting major gas components are: hydrogen; carbon monoxide; air; oxygen; nitrogen; helium; argon; lower mono-olefins, lower diolefins and derivatives thereof; paraffins, such as methane, ethane and the like; and acetylenes. "Olefins" referred to herein are understood to be those selected from the group consisting of mono-olefins having from two to five carbon atoms per molecule, diolefins having four or five carbon atoms per molecule and derivatives thereof. Typical of such olefins are ethylene, propylene, the butylenes, the pentylenes, 1,3-butadiene,1,4-pentadiene and derivatives thereof.

The reacting components are primarily those which form acids in aqueous solutions. These materials react with the alkali of the solvent to form inorganic or organic salts therewith, thereby providing an effective means of their removal from the gas. Examples of acidic or reacting components include hydrogen sulfide, carbon dioxide, carbonyl sulfide, sulfur dioxide, mercaptans, hydrogen chloride, hydrogen cyanide, nitric oxide, and the like.

It has been found in practicing this process that water vapor may be simultaneously removed from the feed gas material even though it is usually present in quantities much higher than trace quantities. The removal of water vapor with the alkali/polyhydric alcohol solution is believed to follow a completely different mechanism from that followed by the removal of the trace quantities of the reacting components of the feed material. The mechanism for water removal may be based on the humectant properties of the polyhydric alcohols. In addition, it is believed that further solution capacity can be effected by such metathesis reactions as:

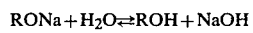

$$RONa + H_2O \rightleftharpoons ROH + NaOH$$

and

$$Na_2CO_3 + H_2O \rightleftharpoons 2NaOH + CO_2$$

It has additionally been found that water removal by the alkali/polyhydric alcohol solution can be effected with respect to contained water in the industrial gas stream which is present up to the limits of saturation in the stream (viz. dew point). The hygroscopicity quality of the polyhydric alcohol which induces water absorption (via hydrogen bonding mechanism) has been found not to diminish capacity of the alkali/polyol solution for reaction of the solution with other reacting components in trace amounts listed above. Thus, such reactions which involve the reacting component in which water can become an equilibrium component seem not to be adversely affected by the presence of such large amounts of water in the solution.

Accordingly, it is understood that any relatively small amount of water vapor contained in the non-reacting gas feed (introduced therein prior to or during a process for the production or treatment of the non-reacting gas) is scavenged by the polyhydric alcohol and alkali of the absorbent solution. Similarly, any water of reaction formed is situ is also scavenged by the alkali solution components as it is formed. Thus, the absorbent solution is characterized herein as an "essentially non-aqueous" solution during the period in the process of the invention when it is acting to effect purification by removal of trace amounts of reacting impurities from the non-reacting gas stream.

It should be noted in passing that the partial pressure of water maintained in the vapor phase above the absorbent solution is lower than that in the non-reacting gas stream (mole basis), so that water is not reintroduced into the non-reacting gas stream.

The typical, non-aqueous absorbent solutions of the invention may initially be prepared by the addition of alkali or alkaline earth metal values to a solution of the selected liquid polyhydric alcohol (glycerol and glycols of the stated group). This addition to the polyhydric alcohol solution may be by the direct addition of alkali metal (such as by the addition of sodium turnings), by the addition of the alkali or alkaline earth metal in the form of its hydroxide, or by the addition of the alkali or alkaline earth metal in the form of its carbonate or bicarbonate, or other similarly weak inorganic acid salts. The addition in the metal or hydroxide or salt form form may react in a desired manner to form the polyhydric alcoholate of the alkali or alkaline earth metal. It may be that a carbonate form is first hydrolyzed by water to the hydroxide before alcoholate formation.

The alkali/polyhydric alcohol solutions are formed by simply mixing the alkali component with the polyhydric alcohol component until a solution of the two components is formed. This can be done at room temperature or at elevated temperatures, viz. temperatures as high as the boiling point of the alcohol. Normally, mixing between the two components is effected at temperatures of from about 30° C. to about 250° C., preferably at temperatures of from about 40° C. to about 220° C.

The alkali value supplied to the polyhydric alcohol may be in the form of the hydroxide, and as salts of weak inorganic acids, viz. carbonic acid. Preferably, the alkali is supplied as the hydroxide, the carbonate and/or the bicarbonate. As pointed out below, the greatest efficiency of impurity removal typically when the alkali is employed as the hydroxide, but that the most stable system is achieved with the carbonate. Illustrative of suitable alkali are, by way of example only, lithium hydroxide, lithium carbonate, lithium bicarbonate, sodium hydroxide, sodium carbonate, sodium bicarbonate, potassium hydroxide, potassium carbonate, potassium bicarbonate, rubidium hydroxide, rubidium carbonate, rubidium bicarbonate, cesium hydroxide, cesium carbonate, cesium bicarbonate, magnesium hydroxide, magnesium carbonate, magnesium bicarbonate, calcium hydroxide, calcium carbonate, calcium bicarbonate, strontium hydroxide, strontium carbonate, barium hydroxide, barium carbonate, and barium bicarbonate.

It has been found that addition of from about 0.5 to 15 weight percent of contained alkali or alkaline earth metal values may be employed to form an operable nonaqueous absorbent solution having a satisfactory contained salt concentration, after reaction with a minor portion of the liquid polyhydric alcohol (glycerol or selected glycol), presuming salt formation. It has additionally been found that elevation to a temperature of the order of about 200° C. is desirable to effect an activation of the carbonate to the hydroxide form. The alkali, in the hydroxide form, may enter in to an equilibrium reaction which generates the alcoholate and a small amount of water. Whether such alcoholates contribute to the process of this invention is hard to determine, but it is believed alcoholate formation plays a significant role.

To develop process design data and to study the characteristics of the column operation, a high-pressure pilot unit was constructed. As Oldershaw type glass column, 28 mm ID, containing 20 trays was employed.

The glass column was mounted in a pressure gauge (Jergusen Co.) for high-pressure operations. The feed gas (ethylene) was preheated to the desired column temperature in a shell-and-tube heat exchanger. Another heat exchanger between the circulating pump and the column was used to control the temperature of the liquid entering the top of the column.

Caustic/glycol solutions were prepared by feeding the desired amounts of sodium hydroxide into the glycol in a mix tank. The solution was stirred at 50°–75° C. under nitrogen purge. Three hours of stirring was sufficient to dissolve the caustic pellets completely. The solution was then transferred to the reservoir section of the Oldershaw column for water stripping. The solution was circulated at 50° C., 50 psig, with nitrogen gas flowing countercurrent to the liquid flow. The stripping was continued until the water concentration in the purge nitrogen decreased below 10 ppm.

The Oldershaw column contained three sample taps to analyze the gas entering and leaving the column. The gas samples was continuously analyzed for $CO_2$ and $H_2O$. Also periodic liquid samples were taken for viscosity determinations.

The column was tested under a variety of operating conditions. These tests can be summarized as follows:

| | |
|---|---|
| Solvents: | Ethylene Glycol |
| | Triethylene Glycol (TEG) |
| Reactants:* | 2% (wt) NaOH |
| | or |
| | 5% (wt) NaOH |
| | 2% Pyrogallol |
| | 2% $MnCl_2$ |
| Feed Gas: | $N_2$ or $C_2H_4$ |
| Column Pressure, psig: | 100–365 |
| Column Temperature, °C.: | 38–60° C. |
| Liquid-to-Gas Mass Flow Ratio: | 0.023–0.167 |
| Gas Velocity, ft/sec.: | 0.15–0.30 |
| $CO_2$ Concentration in Feed Gas, ppm: | 1–110 |
| $H_2O$ Concentration in Discharge Gas, ppm: | 1–1000 |
| $O_2$ Concentration in Feed Gas, ppm: | 0–50 |
| $H_2S$ Concentration in Feed Gas, ppm: | 0–20 |

*Reactant weight percent based on the weight of the total solution.

For good gas-liquid contacting and stable operation, the gas velocity should not exceed the column flooding velocity. Flooding velocities were calculated using a typical correlation for sieve towers for 5 percent NaOH/TEG solutions as set forth in Table I:

TABLE I

FLOODING VELOCITIES FOR OLDERSHAW COLUMN
Solution: 5 percent NaOH/TEG
Gas: $C_2H_4$
Column Diameter: 28 mm

| Liquid-to-Gas Mass Flow Ratio | Column Pressure, psig | Column Temperature, °C. | Flooding Velocity* ft/sec |
|---|---|---|---|
| 0.1 | 300 | 20 | 1.08 |
| 0.2 | 300 | 20 | 0.97 |
| 0.1 | 400 | 20 | 1.13 |
| 0.2 | 400 | 20 | 1.05 |
| 0.1 | 15 | 75 | 5 |
| 0.2 | 15 | 75 | 4.5 |
| 0.1 | 115 | 40 | 1.8 |

*Based on total cross-sectional area of the tower.

For column operation above 250 psig, the calculated flooding velocity is about 1.0 ft/sec. The data base for this correlation consists of mostly industrial operations with aqueous solutions, and thus, liquid viscosity is not included in the correlation. Therefore, its applicability to a viscous medium such as caustic/glycol solutions is uncertain. The pilot unit was operated at gas velocities 0.15 to 0.30 ft/sec. When the gas velocity exceeded 0.7 ft/sec. column operations became unstable. This value corresponds to roughly 60 percent of the calculated flooded velocity, suggesting that the flooding velocity correlations should be adjusted for viscosity.

With both ethylene glycol and triethylene glycol/caustic solutions, tray action was excellent in the indicated operating range.

The results of the $CO_2$ removal experiments are set forth in Table II.

due to decreased NaOH content, a pint of TEG containing 0.1 weight percent $H_2O$ was added to the liquid reservoir and the column was restarted. No improvement in $CO_2$ removal was observed, indicating that the decreased NaOH content was responsible for the decreased column efficiency.

During the lengthy period of continuous operation, three liquid samples were taken for viscosity measurements. No change in viscosity was observed, suggesting the dimerization and oligomerization reactions are insignificant. The same solution was filtered to remove the $Na_2CO_3$ solids, because no noticeable settling occurred in the liquid reservoir. This observation is consistent with settling velocity calculations using the Stokes equation. These calculations show, for example, for a $Na_2CO_3$ particle one micron in diameter, the settling velocity is 0.005 ft/day at 40° C. in 5 percent

TABLE II

$CO_2$ REMOVAL WITH GLYCOL/CAUSTIC SOLUTIONS

| Solvent | NaOH, wt. % | Pressure, psig | Temp., °C. | ** L/G | $U_G$, ft/sec | $H_2O$ Content In the Solution | No. Trays | $CO_2$ Concentration, ppm Feed | $CO_2$ Concentration, ppm Discharge |
|---------|------|-----|----|-------|------|------|----|------|-------|
| EG  | 5 | 100 | 38 | 0.046 | 0.15 | high | 20 | 40   | 0.46  |
| EG  | 5 | 100 | 38 | 0.069 | 0.29 | high | 20 | 80   | 2.0   |
| EG  | 2 | 100 | 55 | 0.023 | 0.29 | high | 20 | 45   | 1.25  |
| EG  | 2 | 100 | 40 | 0.137 | 0.15 | high | 20 | 85   | 1.0   |
| TEG | 5 | 100 | 42 | 0.046 | 0.15 | high | 20 | 95   | 0.50  |
| TEG | 2 | 100 | 52 | 0.069 | 0.29 | high | 10 | 45   | 0.27  |
| TEG | 2 | 100 | 52 | 0.069 | 0.29 | high | 10 | 112  | 0.22  |
| TEG | 2 | 100 | 52 | 0.069 | 0.29 | high | 10 | 50   | 0.12  |
| TEG | 5 | 100 | 50 | 0.167 | 0.13 | high | 10 | 1.1  | 0.20* |
| TEG | 5 | 200 | 51 | 0.109 | 0.15 | low  | 10 | >50  | 0.30* |
| TEG | 5 | 200 | 50 | 0.143 | 0.15 | low  | 10 | >50  | 0.60* |
| TEG | 5 | 240 | 50 | 0.125 | 0.17 | low  | 10 | 43   | 1.60* |
| TEG | 5 | 240 | 53 | 0.05  | 0.21 | low  | 10 | 12   | 3*    |
| TEG | 5 | 365 | 57 | 0.036 |      | low  | 10 | 41   | 1.1   |
| TEG | 5 | 365 | 57 | 0.036 |      | low  | 10 | 13   | 0.65  |

*Same batch running continuously for three weeks.
**In mass units
L/G = liquid-to-gas flow rate ratio
$U_G$ = gas velocity through the column
EG = ethylene glycol
TEG = triethylene glycol Based on these results, the following was concluded:
1. Both ethylene glycol and triethylene glycol/caustic mixtures are very effective for trace $CO_2$ removal. Triethylene glycol, however, is preferred due to its lower vapor pressure.
2. It is possible to reduce the $CO_2$ concentration in ethylene to less than 0.5 ppm with a ten tray column, provided that good gas-liquid contact is maintained.
3. Liquid-to-gas flow rate ratios as low as 0.05 are sufficient for efficient $CO_2$ removal.
4. Five percent NaOH/TEG solutions flow easily at 40°-50° C. with good tray action. The viscosity of this solution at 40° C. is 110 cps.
5. After three weeks of continuous operation with one batch of 5 percent NaOH/TEG solution, no viscosity increase was observed, even though the solution contained the reaction by-product $Na_2CO_3$.
6. No $Na_2CO_3$ solid settling was apparent in the reservoir. However, some solids were trapped in the liquid filters. It appears that the settling velocity is very slow.
7. $CO_2$ removal was equally efficient before and after the water content of the solution was stripped off.

One batch of 5 percent NaOH/TEG solution was operated continuously for three weeks until the $CO_2$ concentration in the column discharge started increasing due to decreased NaOH content relative to the total solution. To test whether the decrease in $CO_2$ removal efficiency is due to lack of free water in the system or NaOH/TEG solution. From scanning electron microscopy measurements, $Na_2CO_3$ particles range in size from 1-10 microns, mostly in the lower size range. These results suggest that a filtration step may be necessary for solids removal.

In addition to the employment of sodium and lithium as alkali metals for the in situ reaction with the selected glycol to form the non-aqueous absorbent solution, tests were conducted to determine the effectiveness of loading various glycolates with various alkaline earth metal hydroxides. The following Tables III and IV show, respectively, the loading of equivalent weight percentages of strontium, barium and calcium hydroxides to diethylene glycol, and the resultant carbon dioxide loss and percentage of theoretical carbon dioxide displaced for nine (9) cycles of regeneration employing these alkaline earth metal hydroxides.

FIG. 3 of the drawings set forth a graphical representation of comparative non-aqueous reversible carbon dioxide scavenging efficiency for barium, calcium, potassium and sodium-based systems through the nine cycles of regeneration. It is to be noted that the sodium-based system presents a consistently high efficiency of operation through all nine cycles.

TABLE III

INITIAL $CO_2$ LOADING IN VARIOUS GLYCOLATES

| Solvent | Solvent Weight, gm | $CO_2$ Uptake, gm |
|---|---|---|
| 5 wt. % $Sr(OH)_2$ in diethylene glycol | 125 | 1.95 |
| 5 wt. % $Ba(OH)_2$ in diethylene glycol | 125 | 2.80 |
| 5 wt. % $Ca(OH)_2$ in diethylene glycol | 125 | 4.50 |

Conditions:
Room temperature
$CO_2$ pressure - atm.

TABLE IV

REGENERATION HISTORY OF ALKALINE EARTH METAL GLYCOLATES

| Solvent | Regeneration Cycle | $CO_2$ Loss, gm | % of Theoretical $CO_2$ Displaced |
|---|---|---|---|
| 5 wt % $Sr(OH)_2$ in diethylene glycol | 1 | 0.8 | 44 |
| | 2 | 0.3 | 17 |
| | 3 | 0.5 | 28 |
| | 4 | 0.9 | 50 |
| | 5 | 0.4 | 22 |
| | 6 | 0.4 | 22 |
| | 7 | 0.4 | 22 |
| | 8 | 0.3 | 17 |
| | 9 | 0.35 | 19 |
| 5 wt % $Ba(OH)_2$ in diethylene glycol | 1 | 0.5 | 39 |
| | 2 | 0.5 | 39 |
| | 3 | 0.35 | 27 |
| | 4 | 0.45 | 35 |
| | 5 | 0.4 | 31 |
| | 6 | 0.5 | 39 |
| | 7 | 0.5 | 39 |
| | 8 | s.45 | 35 |
| | 9 | 0.5 | 39 |
| 5 wt % $Ca(OH)_2$ in diethylene glycol | 1 | 1.5 | 51 |
| | 2 | 1.1 | 37 |
| | 3 | 1.2 | 40 |
| | 4 | 1.05 | 35 |
| | 5 | 1.0 | 34 |
| | 6 | 1.2 | 40 |
| | 7 | 1.0 | 34 |
| | 8 | 0.9 | 30 |
| | 9 | 0.95 | 32 |

Conditions:
$CO_2$ addition at 1 atm and room temperature
Regeneration at 200° C.
Solvent weight - 125 gm In the drawings.

Figure 4:
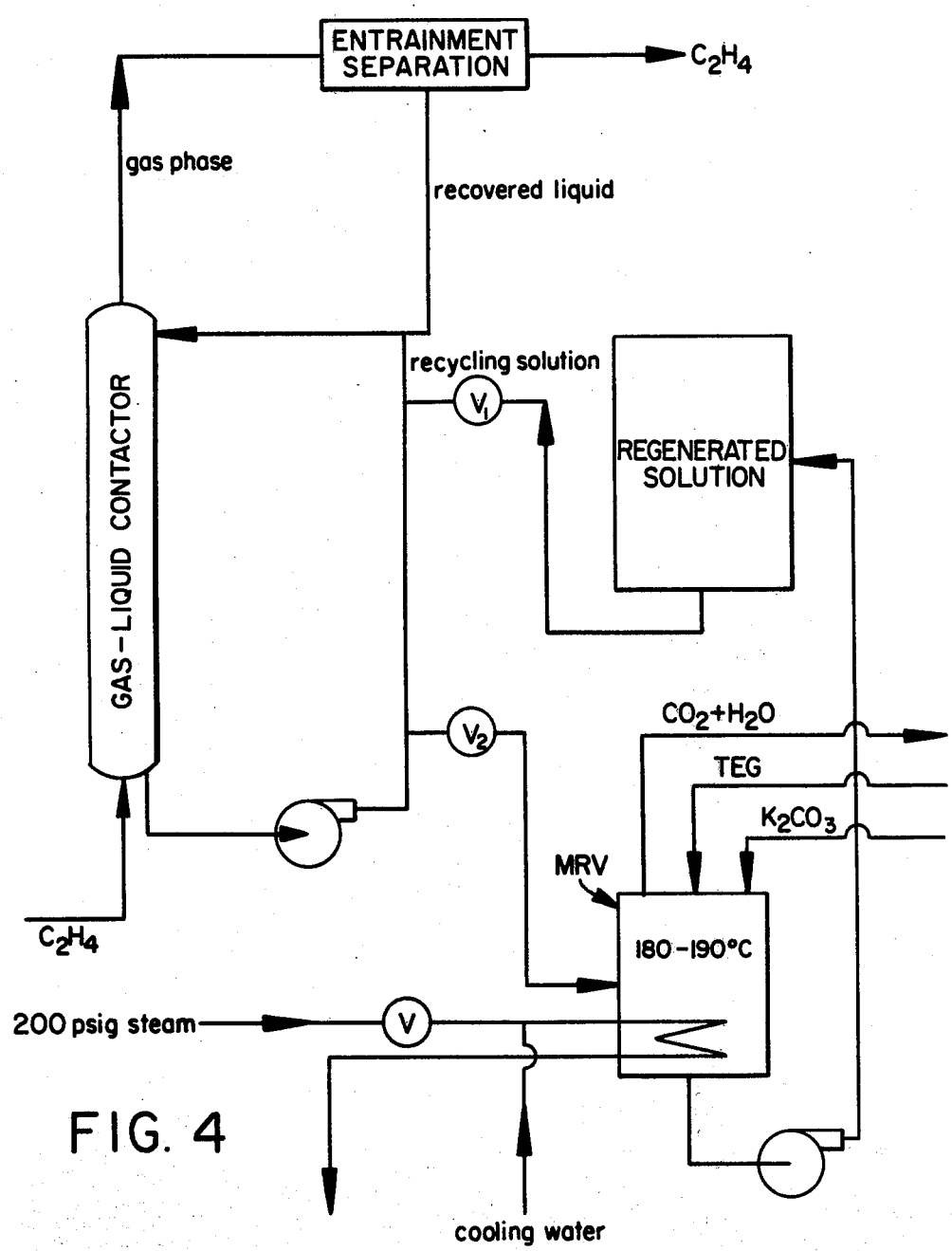
Figure 5:
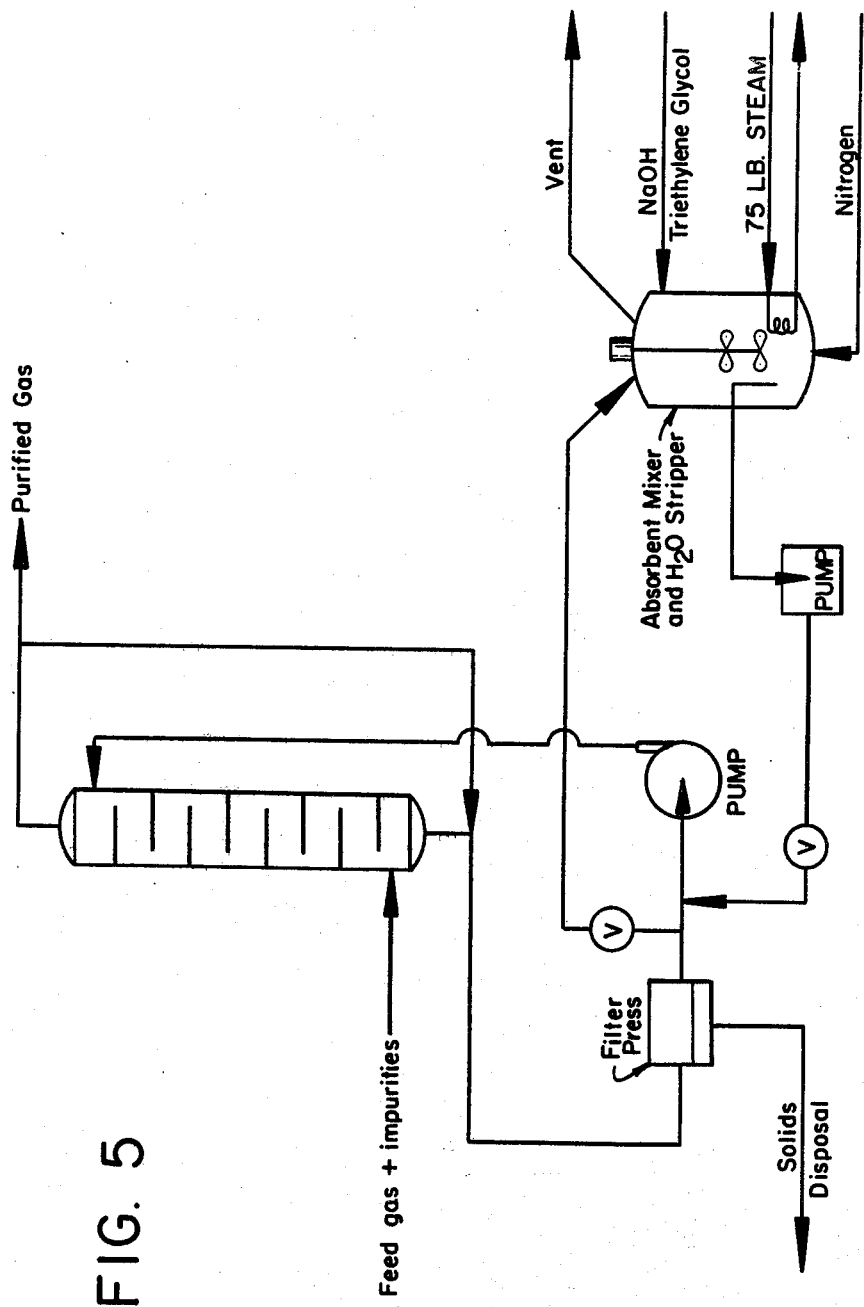

FIG. 4 is a simplified schematic flow sheet for a pilot plant having continuous purification of gas streams with absorbent regeneration wherein no metal carbonate precipitate is formed during operation; and FIG. 5 is a simplified schematic flow sheet for a pilot plant having continuous purification and cyclic regeneration, wherein insoluble metal carbonate precipitate is formed and removed during operation.

Figure 1:
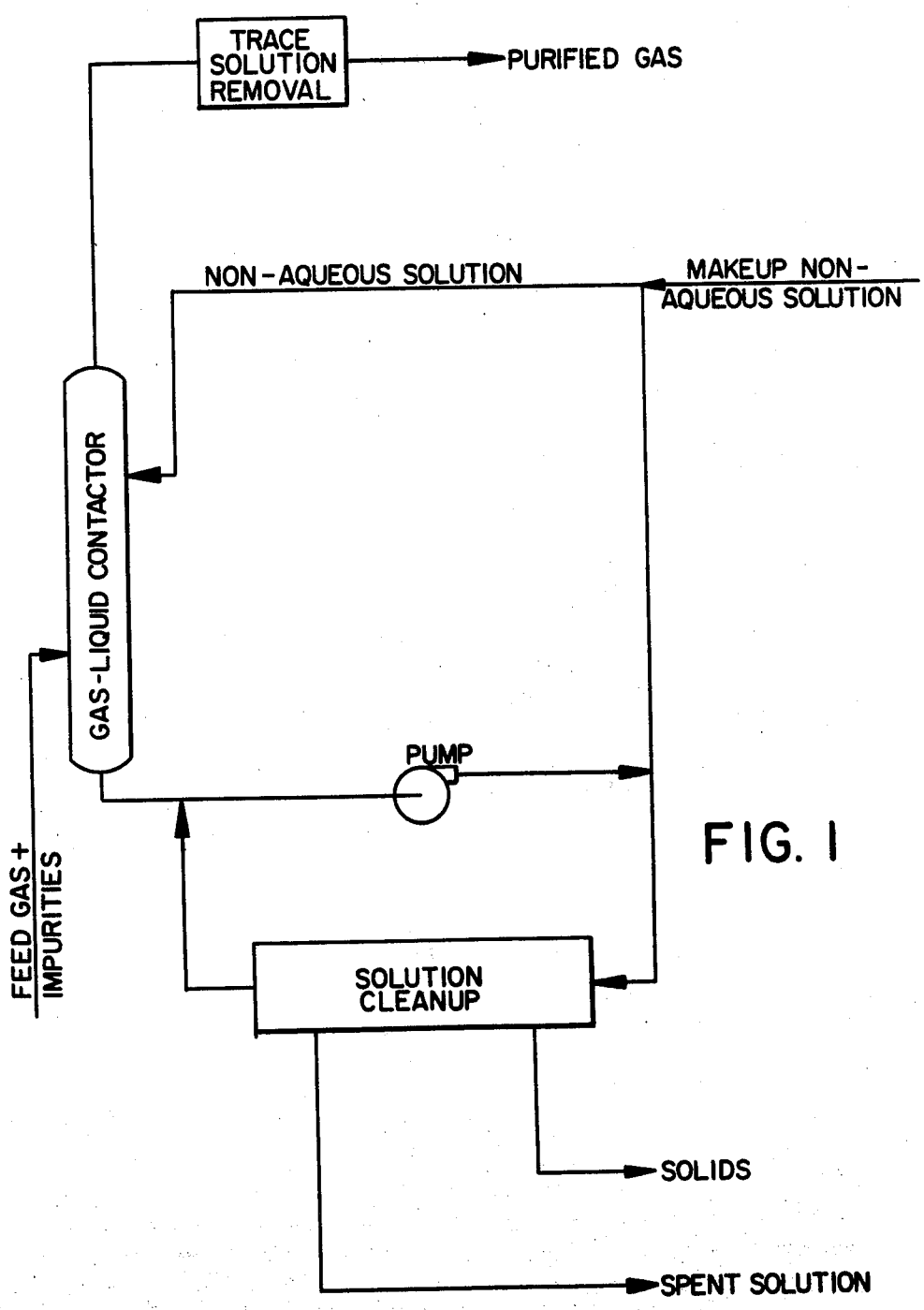
FIG. 1 is a simplified schematic flow sheet of an apparatus arrangement suitable for practicing the process of the invention for gas purification.

Apparatus suitable for commercial operation of the process of the invention is shown schematically in FIG. 1 of the drawings. As there shown, the contacting device may alternatively be a vessel filled with the caustic (NaOH) extractant solution through which the gas stream to be treated is passed.

In the process of the invention, feed gas containing impurities such as $CO_2$, $H_2O$, $SO_2$, $H_2S$, COS and mercaptans, is mixed with a non-aqueous solution in a gas-liquid contactor containing one or more contacting zones. The impurities are removed from the gas by reaction with or dissolution into the solution. If necessary for purity considerations, the purified gas leaving the gas-liquid contactor may be further treated, e.g., by passing through a selective adsorbent bed, to remove traces of the non-aqueous solution.

Depending on the concentration of impurities in the feed and the amount of feed processed, the solution may have to be renewed. This can be done intermittently or continuously by (1) removing solid products of reaction, (2) purging spent solution, and/or (3) separating spent solution and absorbed impurities from active solution. To compensate for any removal of solution by cleanup or by entrainment or vaporization into the purified gas, provision is made for introductions of makeup non-aqueous solution into the process.

A demister may be provided in the top of the column to remove large size spray particles. Ethylene gas leaving the demister passes through a filter which removes sub-micron sized glycol mist. Depending on the size, the liquid can be returned to the stripping still or for small flows it can be collected in a drum and be disposed of periodically. Downstream of the filter, an activated carbon trap may be provided to remove last traces of TEG from ethylene. At 50° C., 450 psig, TEG concentration in ethylene will be less than 0.1 ppm. In the event that TEG removal is desired below that level, it is easily accomplished by adsorption with activated carbon. The TEG loading on activated carbon is expected to be greater than 20 percent by weight. At this loading, 800 pounds of activated carbon is sufficient to completely remove all traces of TEG from a column treating 40,000 lbs/hr ethylene in one year (8000 hrs) of the operation. Therefore, activated carbon can practically be used on a throw-away basis, and no regeneration facilities are needed to allow reasonably economical operation.

A double filter arrangement may be provided to remove the carbonate solids from the solution. The caustic/glycol solution leaving the filters is separated into two streams. Approximately 20 percent of the flow is depressurized to 20 psig and routed to the stripping still, and the remaining 80 percent is circulated to the top of the absorber via the circulating pump. For a column treating 40,000 lbs/hr ethylene, liquid flow should be at least 10 gallon/min (L/G=0.125).

The stripping still operates at 10–20 psig, 100° C., and it has two primary functions:

1. To decrease the moisture content of the fresh caustic/glycol solutions to less than 10 ppm in the gas phase. This is accomplished by nitrogen purging at 100° C. intermittently when makeup solid caustic is added to the system.

2. To remove the moisture adsorbed by the circulating solution with continuous nitrogen purging at 100° C. With this mode of operation, the caustic/glycol solution will remove $CO_2$ by reaction and $H_2O$ by physical adsorption. Since the moisture content of the incoming ethylene is small (~5 ppm), only a small portion of the circulating solution needs to be desorbed. The still should be sized to hold 120 gallons of 10 percent NaOH/TEG solution.

The stripping still is equipped with a turbine-type agitator to dissolve the solid caustic in glycol solutions. As NaOH is removed from the system by reaction with $CO_2$, fresh sodium hydroxide must be added. To add solid caustic, the still is depressurized and purged with nitrogen, the tank is opened and flake caustic is added to bring the solution to, for example, 15 percent NaOH. After the moisture content in the purge nitrogen is below 10 ppm this concentrated stream is gradually mixed with the circulating solution. During the solid caustic addition and moisture removal step, all of the liquid leaving the filters is circulated to the column with no side flow to the stripper.

The heat source for the still can be low-pressure steam on the jackets. It should be capable of heating the solution to 150° C., although a maximum of 100° C. is sufficient for efficient moisture removal.

The following Table V sets forth typical examples of the practice of the process of the present invention employing varying feed gases, sodium and potassium-based absorbent systems, flow rates and operating temperatures employed.

From the examples set forth herein, it may be seen that, in the process of the present invention, bulk quantities (major proportions of the absorbent) of the glycol/glycolate solution are employed to effect gas purification (of nitrogen or ethylene) by reduction of impurities such as carbon dioxide, carbonyl sulfide, and hydrogen sulfide from a relatively high concentration level to a low parts per million level.

The inlet carbon dioxide range over the period was 1–6 ppm and the outlet carbon dioxide range was 0.05–0.15 ppm. The ethylene feed was 30 pounds per hour and the gas velocity in the scrubber was 0.6 feet per minute. The scrubber in the final days of operation was found to reduce an inlet carbon dioxide impurity in the gas stream of 5.35 ppm to an outlet content of 0.10 ppm.

In the initial experimental practice of the process of the invention, a sodium-based system was investigated wherein the absorbent solution was prepared by addition of sodium hydroxide or carbonate, or metallic sodium to the excess glycol or glyceride solution to provide the desired sodium glycol or glyceride salt in unreacted glycol or glycerol solvent.

The process of such sodium-based system can present a problem in stream processing. When employing absorbent solutions based on NaOH and a liquid polyhydric alcohol, there may arise the need for filtration of the spent solution to effect removal of very fine (1–40 microns) $Na_2CO_3$ solids produced when any moisture is present. The process of the sodium-based system also presents the inherent limitation (when not further treated) of being a one-shot, non-continuous process in terms of the caustic employed.

It has been found that a potassium-based absorbent system, as described hereinbelow, provides advantages over the sodium-based absorbent system. The non-aqueous absorbent solution is a potassium glycolate or glycerate formed by the reaction of either elemental potassium, potassium hydroxide or potassium carbonate with the polyol, e.g., glycol and/or glycerol. When the preferred potassium carbonate is employed as the source of potassium, a thermal activation step at about 200° C. is desired for optimization of alcoholate formation.

TABLE V

| System Wt % | Caustic/Solvent | Feed Gas+ ppm/gas | Feed Flow Rate-SCFH | Scrubber Temp. °C. | Impurity Remaining (ppm) | Remarks | |
|---|---|---|---|---|---|---|---|
| 10% | NaOH/glycerol | $10^4$ $CO_2/N_2$ | | 60 | 0.2–0.5 | Tube with steel wool baffles | |
| 10% | NaOH/ethylene glycol | $10^4$ $CO_2/N_2$ | | 25 | 0.2–0.4 | Tube with steel wool baffles | |
| 20% | NaOH/ethylene glycol | $10^4$ $CO_2/N_2$ | | 60 | 0.3–0.5 | Tube with steel wool baffles | |
| 5.04% | NaOH*/Tri-ethylene glycol | 500 $CO_2/N_2$ | 24 | 75 | <1 | Oldershaw column, 20 trays | |
| 5% | NaOH/Triethylene glycol | 500 $CO_2/N_2$ | 27 | 75 | <1 | Oldershaw column, 10 trays | |
| 5% | NaOH/Triethylene glycol | 500 $CO_2/N_2$ | 13 | 75 | <1 | Oldershaw column, 10 trays | ** |
| 2% | NaOH/Triethylene glycol | 500 $CO_2/N_2$ | 27 | 75 | 3 | Oldershaw column, 20 trays | |
| | | | 13 | 75 | 1.5 | Oldershaw column, 20 trays | |
| 2% | NaOH/Triethylene glycol | 500 $CO_2/N_2$ | 27 | 75 | 5 | Oldershaw column, 10 trays | |
| 20% | KOH/ethylene glycol | $10^3$ $CO_2/C_2H_4$ | | | <1 | | |
| 20% | KOH/ethylene glycol | $10^3$ $COS/C_2H_4$ | | 25 | 17–25 | Tube with steel wool baffles | |
| 20% | KOH/ethylene glycol | $10^3$ $H_2S/C_2H_4$ | | | <1 | | |

*Added as 2.9% Na metal.
**Liquid flow in column, 100 g/hr.
+Feed gas pressure-atmospheric In a pilot plant of the type shown in the flow sheet of FIG. 5 of the drawings, an on-stream example of the purification process of the invention was carried out. A preliminarily purified ethylene stream from a commercial ethylene production facility was passed for a period of 56 days through a non-aqueous absorbent solution containing 6% sodium hydroxide (94% triethylene glycol) in a non-aqueous scrubber. The scrubber temperature was 30° C. and the ethylene feed pressure 450 psig.

The continuous system is typified by the thermal regeneration of a potassium-based glycolate or glycerate containing solution which are used to scavenge $CO_2$ from a variety of feed streams. It has been found that $K_2CO_3$ dissolved in glycol solutions is quite soluble up to concentrations of about 10 weight pecent at ambient temperatures or slightly above (viz. 20°–25° C.). It also has been found that, when these $K_2CO_3$-continuous solutions are heated to ~180°-200° C., the $K_2CO_3$ decomposes to release $CO_2$ with the simultaneous formation of a potassium glycolate salt.

The reaction is believed to be:

$$K_2CO_3 + 2ROH \xrightarrow[(180-200° C.)]{N_2} 2ROK + H_2O + CO_2 \quad (A)$$

wherein ROH represents any glycol. The potassium glycolate salt, ROK, is therefore of the same species as if it were initially produced from KOH, as follows:

$$ROH + KOH \xrightarrow[(125° C.)]{N_2} ROK + H_2O \quad (B)$$

When ROK is formed in the presence of water, due to the use of KOH as the alkali metal source material (see Equation B) the $H_2O$ is scavenged from the system at the regenerator by displacement with $N_2$ gas.

Upon $CO_2$ scavenging in the absence of water, the reaction is believed to be as follows:

$$ROK + CO_2 \xrightarrow[(25-100° C.)]{} RO-\overset{\overset{O}{\|}}{C}-OK \quad (C)$$

The product, $$RO-\overset{\overset{O}{\|}}{C}-OK,$$

is also soluble in the excess glycol solvent and will also decompose at 180°-200° C. to split out $CO_2$, thus regenerating the ROK salt for re-use. If trace quantities of water enter the scrubber with the feed it is believed that the inorganic carbonate $K_2CO_3$ will be formed, but unlike the $Na_2CO_3$ which would be present as a solid, $K_2CO_3$ remains in solution and can again be thermally regenerated. Hence, the advantage of this aspect of the invention is that under the indicated conditions no precipitate will form and all carbonate species formed can be thermally decomposed, thus providing a reactivated $CO_2$ scavenging solution after proper cooling before it is returned to the scrubber section.

This aspect of the invention, therefore, provides a thermally regenerable $CO_2$ scavenging system without the need for filtration equipment.

The KOH-$K_2CO_3$/glycol process for $CO_2$ removal is based on the use of stable non-aqueous solvents, such as triethylene glycol, with low vapor pressure and with high dissolving capacity.

The chemistry of KOH-$K_2CO_3$/glycol solutions is not entirely understood at present. It is not believed that potassium carbonate is simply physically dissolved in glycols. According to our best understanding, some reactions between the alkali and, e.g., triethylene glycol (TEG) is achieved; probably a partial alcoholation is effected.

Commercially available triethylene glycol (TEG) contains about 0.1 percent (weight) water. In addition, KOH/TEG reactions form water. Therefore, when a glycolate or glycerate is prepared, the mixture will contain some water after preparation. This water is typically stripped away, prior to use of the solution for impurities removal. During the stripping operation, the equilibrium will continuously shift to the right as the water is removed from the system favoring alcoholate formation. If the major portion of the water is removed from the system, the solution will contain potassium glycolate, unreacted glycol and small amounts of free unreacted KOH and/or $K_2CO_3$ (if used as a starting material). The KOH/glycol solutions are extremely hygroscopic and there will be some chemically condensed water complexed with the excess glycol and remain in the solution even following the drying step. This water is removed from the system by heating and purging with an inert gas or by an equivalent means and is not permitted to accumulate. However, such water removal is not critical to the invention. Thus, the KOH/glycol solutions also can function as water scavengers.

Table V hereinabove sets forth typical examples of the practice of the process of the invention employing varying feed gases, NaOH and KOH/solvent systems, flow rates and operating temperatures employed.

From the examples set forth, it may be seen that, in the process of the invention, bulk quantities (major proportions of the absorbent) of the glycol/glycolate solution are employed to effect gas purification (of nitrogen or ethylene) by reduction of impurities such as carbon dioxide, carbonyl sulfide, and hydrogen sulfide from a relatively high concentration level to a low parts per million level.

The use of the potassium-based system adds improved water scavenging capabilities simultaneously with its application as $CO_2$ scavenger, such being accomplished without solids forming. In case of the ethylene feed which also contains trace amounts of water, this system eliminates the need for water-removing adsorbents or at least reduces their size considerably. One ideal application is for the removal of atmospheric $CO_2$ and $H_2O$ from air feed in the production of $N_2$ and $O_2$ by cryogenic air separation.

Figure 2:
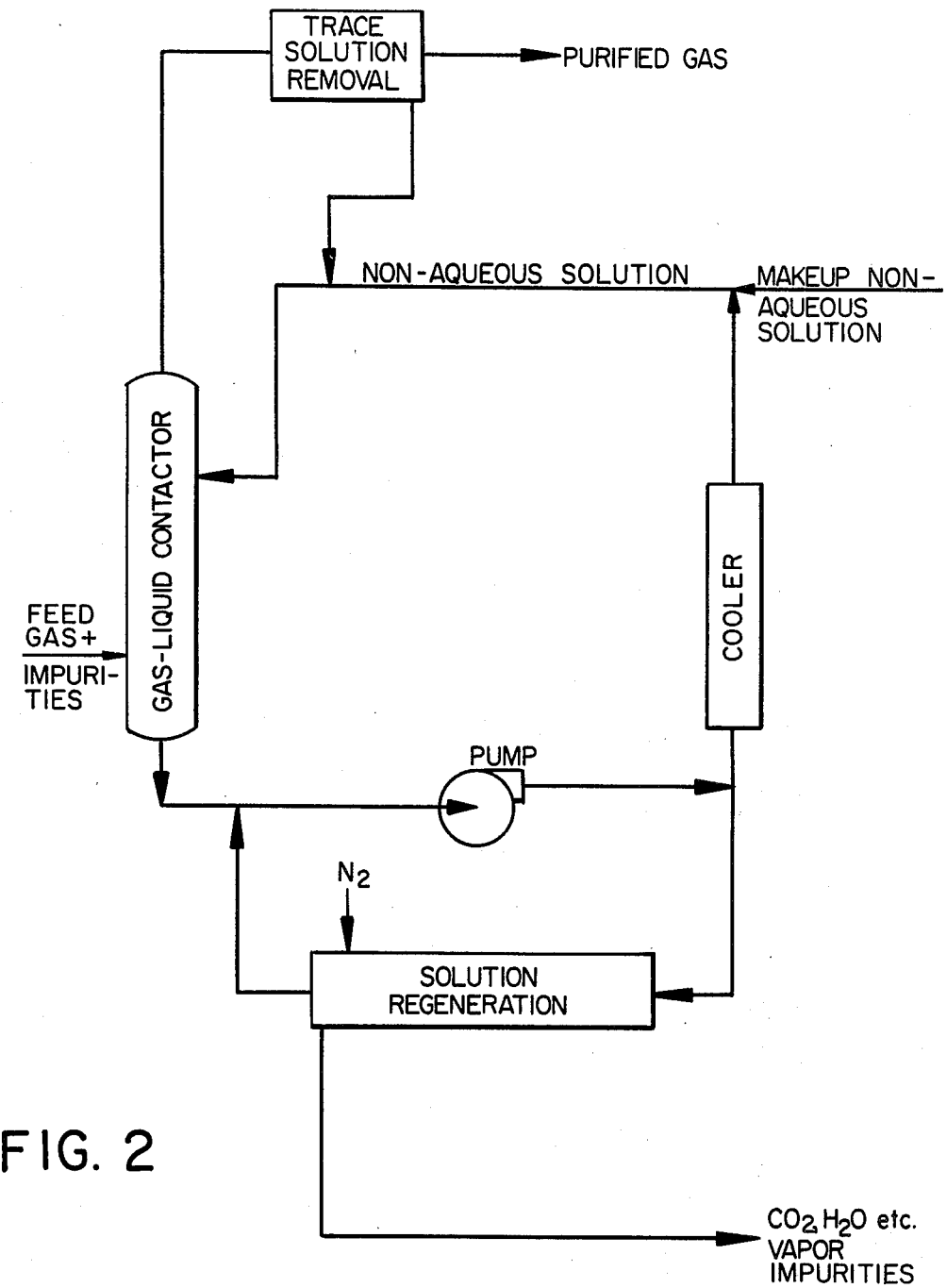
FIG. 2 is a schematic flow sheet of an apparatus arrangement similar to that of FIG. 1 and additionally having means for the regeneration of spent non-aqueous absorbent solution and recycling the regenerated solution to the liquid-gas contactor for further use.
Figure 3:
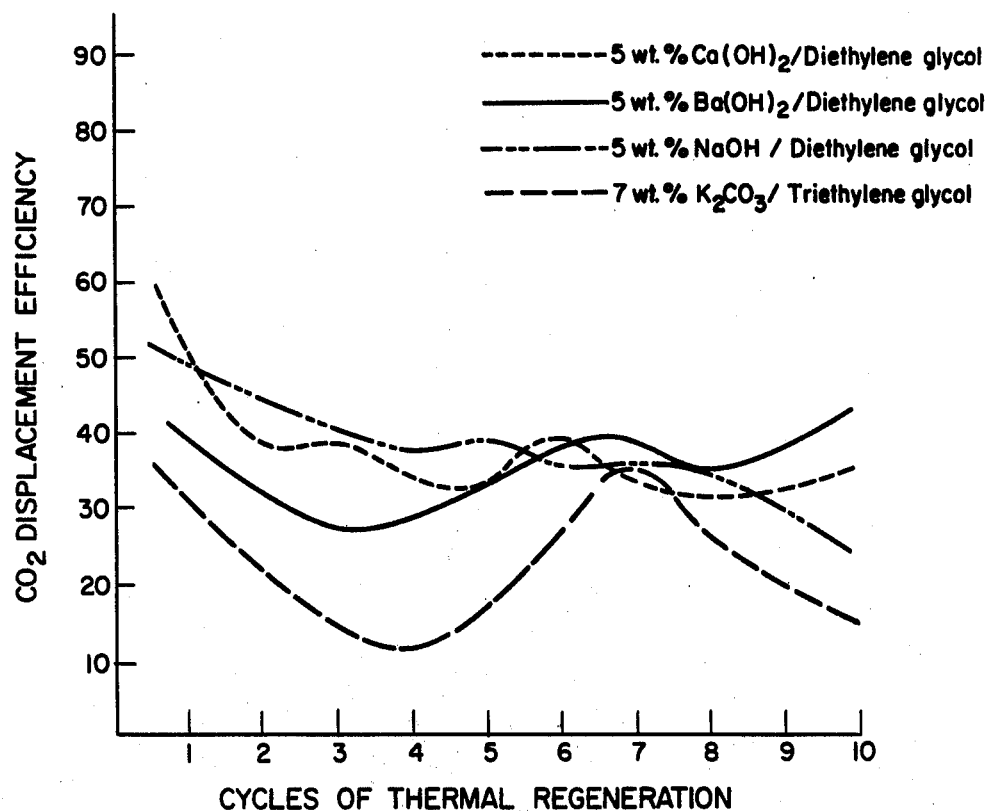
FIG. 3 is a curve showing the carbon dioxide displacement efficiency for a number of cycles of thermal regeneration of four different alkali or alkaline earth metal based scavenging systems.

As discussed hereinabove, the spent non-aqueous absorbent solution is regenerated in the cyclic process as is graphically shown in the flow sheet of FIG. 2 of the drawings. As there shown, a nitrogen gas purge is employed in the solution regeneration step in combination with heating to a temperature of about 180°-200° C. to decompose (to carbon dioxide) the carbonate formed in the solution and remove the carbon dioxide along with water vapor and other vapor impurities which are released and purged.

As indicated hereinabove, the flow sheet set forth in FIG. 4 of the drawings shows cycle embodying the process of the invention for the potassium-based system or any other system in which insoluble, solid carbonate precipitate is not formed in the absorbent solution. As there shown, valves V1 and V2 would be open only for a fraction of daily, continuous operation. The cycle will permit a batch or continuous regeneration operation. If continuous, a cooler is required in the line between the makeup and regeneration vessel and the storage vessel. It is to be noted that the solution is cooled in the regeneration vessel prior to transfer to the storage vessel. The embodiment of this figure of the drawings is designed to operate for the purification of ethylene, employing 6% by weight $K_2CO_3$ feed in triethylene glycol solution. The use of nitrogen purge gas for evolved $CO_2$ and other vapor impurities is optional with this potassium-based system.

The use of a sodium-based non-aqueous absorbent solution for extended time periods can result in the formation of fine sodium carbonate precipitate particles (of the order of 1-40 microns in size), making the removal of the precipitate merely by employment of a filtration step more difficult. It has been determined that such fine precipitate may be agglomerated into particles of larger size (of the order of 200-400 microns) by a number of alternative processing steps. Such larger precipitate particles can then be removed from the solution by the use of a simple direct filtration step, as indicated in the embodiment of apparatus shown in FIG. 5 of the drawings.

This agglomeration can be effected by any one of a number of procedures such as: the addition of up to 15% by weight of water prior to heat treatment at about 150° C.; and the addition of up to 2% by weight of common ion addition (e.g., sodium chloride for chloride ion), with or without up to about 5% by weight water. Such additions to the cycle to effect agglomeration are not shown in the simplified flow sheet of FIG. 5 but may be made along with the use of a related heater in the line immediately upstream of the filter press.

The NaOH-based non-aqueous scrubber has the disadvantage that a precipiate, $Na_2CO_3$, tends to accumulate under certain operating conditions. However, the NaOH-based non-aqueous scrubber is still more attractive when compared to the NaOH solid pellet absorber system. As indicated hereinabove, it was found that the use of the $K_2CO_3$-based non-aqueous scrubber resulted in a thermally regenerable system. The $K_2CO_3$ system has two distinct advantages over the NaOH system in that it is free of precipitation of solids upon $CO_2$ cycling and it is more thermally stable. However, the $K_2CO_3$ has only about half the chemical efficiency as the NaOH system for cyclic $CO_2$ scavenging. Earlier studies indicated that NaOH-based systems can displace approximately 42% of the theoretical amount of $CO_2$ absorbed while $K_2CO_3$-based systems displace approximately 20% $CO_2$.

Table VI summarizes the results of cyclic $CO_2$ scrubbing using solutions consisting of 3 weight percent LiOH dissolved in diethylene, triethylene, and dipropylene glycol. Theoretically, 5.5 grams of $CO_2$ can be absorbed by 100 grams of 3 weight percent LiOH in these solvents, based on the organic carbonate stoichiometry. Using 5.5 grams as a figure for total $CO_2$ absorption, one can calculate theoretically the percent $CO_2$ displaced for each $CO_2$ absorption/desorption cycle. Through five cycles of $CO_2$ absorption/desorption, 3 weight percent LiOH/diethylene glycol theoretically displaced an average 14.7% of the theoretical amount of $CO_2$ per cycle while the LiOH-based solutions of dipropylene and triethylene glycol respectively, displaced an average 15.7 and 14.3% of the theoretical amount of $CO_2$ per cycle. From a standpoint of efficient $CO_2$ displacement, this study shows there is little if any significance in selecting one LiOH-based glycol solution in preference to another. Furthermore, from Table VI, it is seen that $CO_2$ displacement (i.e., chemical) efficiency declined drastically with each succeeding cycle of $CO_2$ absorption/desorption, regardless of glycol selection. For comparative purposes, Table VII shows the results for NaOH, $K_2CO_3$ and LiOH-based non-aqueous solutions of diethylene glycol. From Table VII the NaOH-based, non-aqueous scrubber appears to have superior chemical efficiency compared to $K_2CO_3$ and LiOH-based non-aqueous scrubbers. This conclusion is supported by the fact that after five cycles of $CO_2$ cycling, NaOH theoretically displaces a mean value of 42.0% of the theoretical amount of $CO_2$ per cycle while $K_2CO_3$ and LiOH-based non-aqueous scrubbers displace 19.9 and 17.4%, respectively, per cycle.

TABLE VI

NON-AQUEOUS REVERSIBLE $CO_2$ SCAVENGING USING 3 WT. % LiOH IN GLYCOL SOLVENTS (REGENERATION TEMPERATURES 200° C.)

| Solvent | Regeneration Cycle | $CO_2$ Loss (grams) | Theoretical % $CO_2$ Displaced | |
|---|---|---|---|---|
| Diethylene glycol | 1 | 1.60 | 29.1 | Theoretical % $CO_2$ displaced after 5 cycles $\overline{X}$ = 17.4% |
| | 2 | 1.30 | 23.6 | |
| | 3 | 1.10 | 20.0 | |
| | 4 | 0.50 | 9.09 | |
| | 5 | 0.30 | 5.45 | |
| Triethylene glycol | 1 | 1.00 | 18.2 | Theoretical % $CO_2$ displaced after 5 cycles $\overline{X}$ = 14.3% |
| | 2 | 0.90 | 16.3 | |
| | 3 | 0.90 | 16.3 | |
| | 4 | 0.60 | 10.9 | |
| | 5 | 0.55 | 10.0 | |
| | 6 | 0.60 | 10.9 | |
| | 7 | 0.90 | 16.3 | |
| | 8 | 0.40 | 7.27 | |
| Dipropylene glycol | 1 | 0.90 | 16.3 | Theoretical % $CO_2$ displaced after 5 cycles $\overline{X}$ = 15.9% |
| | 2 | 1.10 | 20.0 | |
| | 3 | 1.00 | 18.2 | |
| | 4 | 0.90 | 16.3 | |
| | 5 | 0.50 | 9.09 | |
| | 6 | 0.60 | 10.9 | |
| | 7 | 1.03 | 18.7 | |
| | 8 | 0.50 | 9.09 | |

TABLE VII

COMPARATIVE NON-AQUEOUS REVERSIBLE $CO_2$ SCAVENGING EFFICIENCY FOR Na, K, AND Li BASED SYSTEMS

| Caustic | Solvent | Regeneration Cycle | $CO_2$ Loss Grams | Theoretical % $CO_2$ Displaced | Theoretical % $CO_2$ Displaced $\overline{X}$ Value |
|---|---|---|---|---|---|
| 5 Wt. % NaOH | Diethylene glycol | 1 | 2.70 | 49.1 | 42.0 |
| | | 2 | 2.45 | 44.5 | |
| | | 3 | 2.20 | 40.0 | |
| | | 4 | 2.00 | 36.4 | |
| | | 5 | 2.20 | 40.0 | |
| 7 Wt. % $K_2CO_3$ | Diethylene glycol | 1 | 0.74 | 16.6 | 19.9 |
| | | 2 | 1.67 | 37.4 | |
| | | 3 | 0.84 | 18.8 | |
| | | 4 | 0.99 | 22.2 | |
| | | 5 | 0.20 | 4.48 | |
| 3 Wt. % LiOH | Diethylene glycol | 1 | 1.60 | 29.1 | 17.4 |
| | | 2 | 1.30 | 23.6 | |
| | | 3 | 1.10 | 20.0 | |
| | | 4 | 0.50 | 9.07 | |
| | | 5 | 0.30 | 5.45 | |

What is claimed is:

1. The process for the purification of an industrial gas stream of one or more of hydrogen, carbon monoxide, air, nitrogen, oxygen, helium, argon, mono-olefins having from two to five carbon atoms per molecule, diolefins having four or five carbon atoms per molecule, paraffins and acetylenes, by the removal of trace amounts of impurities therein, of one or more of water, hydrogen sulfide, carbon dioxide, carbonyl sulfide, sulfur dioxide, hydrogen chloride, hydrogen cyanide, nitric acid, and mercaptans which process comprises the steps of: providing a liquid essentially non-aqueous solution comprising from about 0.5 to about 15 weight percent of at least one member selected from the group consisting of alkali and alkaline earth metal, present as a hydroxide or a carbonate, in a liquid aliphatic polyhydric alcohol having a carbon to oxygen ratio of one to about five, and at least two oxygens thereof being separated by not more than two sequential carbon atoms;

heat treating said solution to remove water originally in the solution as well as water formed by natural hygroscopic reaction with said alcohols and by the reaction:

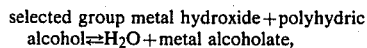

as well as the following reaction to activate said solution (if a carbonate is selected):

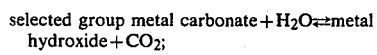

stripping the resultant solution to remove the water, effecting purification by contacting said industrial gas, at a temperature between about 15° and 100° C., with the stripped solution; and separating the purified industrial gas from the reaction products of said contacting step.

2. The process in accordance with claim 1, wherein said gas stream contains dissolved water vapor in an amount up to its limit of saturation therein, said water vapor being concurrently removed from said gas stream with other of such impurities.

3. The process in accordance with claim 1, wherein the concentration of said alkali metal is from 1 to 10 weight percent.

4. The process in accordance with claim 1, wherein the alkali or alkaline earth metal is sodium or potassium provided as the hydroxide.

5. The process in accordance with claim 4, wherein said alkali metal hydroxide is sodium hydroxide.

6. The process in accordance with claim 1, wherein said alkali metal or alkaline earth metal is potassium provided as the hydroxide or carbonate.

7. The process in accordance with claim 1, wherein the selected gas is ethylene.

8. The process in accordance with claim 1, wherein the selected polyhydric alcohol is triethylene glycol.

9. The process in accordance with claim 1, wherein said stream is continuously fed to a liquid body of said solution, the gas stream is removed from contact with said into an atmosphere contiguous with said body in which the partial pressure of water vapor therein is insufficient to significantly increase the water concentration in said stream.

10. The process in accordance with claim 9, wherein the water concentration in said stream leaving said body and said atmosphere is less than that contained in the stream fed to the body.

11. The process in accordance with claim 10, wherein the alkali and alkaline earth metal is potassium provided as a carbonate.

12. The process in accordance with claim 1, wherein said contacting involves countercurrently passing said stream through said solution.

* * * * *